(12) United States Patent
Wang et al.

(10) Patent No.: US 11,448,778 B2
(45) Date of Patent: Sep. 20, 2022

(54) NEURAL NETWORK-BASED CORRECTOR FOR PHOTON COUNTING DETECTORS

(71) Applicant: RENSSELAER POLYTECHNIC INSTITUTE, Troy, NY (US)

(72) Inventors: Ge Wang, Loudonville, NY (US); Ruibin Feng, Troy, NY (US); David Rundle, Butler, PA (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 16/770,675

(22) PCT Filed: Dec. 7, 2018

(86) PCT No.: PCT/US2018/064468
§ 371 (c)(1),
(2) Date: Jun. 8, 2020

(87) PCT Pub. No.: WO2019/113440
PCT Pub. Date: Jun. 13, 2019

(65) Prior Publication Data
US 2020/0408929 A1 Dec. 31, 2020

Related U.S. Application Data

(60) Provisional application No. 62/775,067, filed on Dec. 4, 2018, provisional application No. 62/596,304, filed on Dec. 8, 2017.

(51) Int. Cl.
*G06K 9/00* (2022.01)
*G01T 1/17* (2006.01)
(Continued)

(52) U.S. Cl.
CPC ............... *G01T 1/17* (2013.01); *G01T 1/18* (2013.01); *G06T 7/0012* (2013.01);
(Continued)

(58) Field of Classification Search
CPC .......... G01T 1/17; G01T 1/18; G06T 7/0012; G06T 2207/10116; G06T 2207/20081;
(Continued)

(56) References Cited

U.S. PATENT DOCUMENTS

| | | | | |
|---|---|---|---|---|
| 7,545,965 B2* | 6/2009 | Suzuki | ................. | G06T 7/0012 382/128 |
| 10,078,009 B2* | 9/2018 | Daerr | ..................... | G01T 1/171 |

(Continued)

OTHER PUBLICATIONS

Touch, M., et al., "A neural network-based method for spectral distortion correction in photon counting x-ray CT," Physics in Medicine & Biology, vol. 61,2016, pp. 6132-6153 (Year: 2016).*

(Continued)

*Primary Examiner* — Van D Huynh
(74) *Attorney, Agent, or Firm* — Murtha Cullina LLP; Anthony P. Gangemi

(57) ABSTRACT

A neural network based corrector for photon counting detectors is described. A method for photon count correction includes receiving, by a trained artificial neural network (ANN), a detected photon count from a photon counting detector. The detected photon count corresponds to an attenuated energy spectrum. The attenuated energy spectrum is related to characteristics of an imaging object and is based, at least in part, on an incident energy spectrum. The method further includes correcting, by the trained ANN, the detected photon count to produce a corrected photon count. The method may include reconstructing, by image reconstruction circuitry, an image based, at least in part, on the corrected photon count.

38 Claims, 5 Drawing Sheets

(51) Int. Cl.
  *G01T 1/18* (2006.01)
  *G06T 7/00* (2017.01)
  *A61B 6/00* (2006.01)
(52) U.S. Cl.
  CPC ... *A61B 6/4241* (2013.01); *G06T 2207/10116* (2013.01); *G06T 2207/20081* (2013.01); *G06T 2207/20084* (2013.01); *G06T 2207/30004* (2013.01); *G06T 2207/30242* (2013.01)
(58) Field of Classification Search
  CPC . G06T 2207/20084; G06T 2207/30004; G06T 2207/30242; A61B 6/4241
  USPC .......................................................... 382/132
  See application file for complete search history.

(56) References Cited

U.S. PATENT DOCUMENTS

| | | | | |
|---|---|---|---|---|
| 11,029,425 | B2* | 6/2021 | Steadman Booker | G01T 1/247 |
| 2010/0074397 | A1* | 3/2010 | Kappler | G01T 1/24 |
| | | | | 378/19 |
| 2015/0078512 | A1* | 3/2015 | Goderer | G01N 23/046 |
| | | | | 378/207 |
| 2015/0146844 | A1* | 5/2015 | Zamyatin | A61B 6/032 |
| | | | | 378/5 |
| 2015/0178958 | A1* | 6/2015 | Zou | A61B 6/4241 |
| | | | | 378/19 |
| 2016/0135774 | A1* | 5/2016 | Ono | A61B 6/032 |
| | | | | 378/5 |
| 2016/0328643 | A1* | 11/2016 | Liu | G06N 3/0454 |
| 2018/0192977 | A1* | 7/2018 | Jin | A61B 6/5282 |
| 2019/0008474 | A1* | 1/2019 | Sjolin | A61B 6/585 |
| 2019/0162679 | A1* | 5/2019 | Yamakawa | G01V 5/0016 |
| 2020/0390413 | A1* | 12/2020 | Roessl | G01T 1/17 |

OTHER PUBLICATIONS

International Search Report and The Written Opinion of the International Searching Authority, International Application No. PCT/US2018/064468, dated Feb. 25, 2019.

Touch, M., et al., "A neural network-based method for spectral distortion correction in photon counting x-ray CT," Physics in Medicine & Biology, vol. 61, 2016, pp. 6132-6153.

* cited by examiner

NEURAL NETWORK-BASED CORRECTOR FOR PHOTON COUNTING DETECTORS

CROSS REFERENCE TO RELATED APPLICATION(S)

This application claims the benefit of U.S. Provisional Application No. 62/596,304, filed Dec. 8, 2017, and U.S. Provisional Application No. 62/775,067, filed Dec. 4, 2018, which are both incorporated by reference as if disclosed herein in their entirety.

FIELD

The present disclosure relates to a corrector for photon counting detectors, in particular to, a neural network-based corrector for photon counting detectors.

BACKGROUND

X-rays have played a significant role in modern diagnostic medicine since they were first produced and detected by Wilhelm C. Roentgen in 1895. X-ray detection technology in most current x-ray scanners utilizes energy integrating detectors (EIDs). EIDs are configured to integrate electrical signals generated from interactions between an x-ray beam and detection materials over an entire energy spectrum. Thus, energy-dependent information may be lost and the generated linear attenuation coefficients may not be tissue-type specific. The performance of EIDs may be degraded due to dark current (i.e., electric noise) and Swank noise. Lower energy photons, which carry more contrast information, may receive lower weights due to beam hardening.

Photon counting detectors (PCDs) may be utilized for medical x-ray imaging. PCDs recognize photons both individually and spectrally with multiple energy windows. With their energy discrimination capabilities, PCDs can reveal the elemental composition of materials and distinguish more than one contrast medium simultaneously. Novel contrast agents such as gold nanoparticles (GNPs) also become applicable with PCDs. PCDs have a higher signal-to-noise ratio (SNR) than EIDs since the dark current and Swank noise may be suppressed and do not affect either the output signal intensity or the counts in energy windows. The weights of x-ray photons are not biased in photon counting detectors.

SUMMARY

In some embodiments, a method for photon count correction includes receiving, by a trained artificial neural network (ANN), a detected photon count from a photon counting detector. The detected photon count corresponds to an attenuated energy spectrum. The attenuated energy spectrum is related to characteristics of an imaging object and is based, at least in part, on an incident energy spectrum. The method further includes correcting, by the trained ANN, the detected photon count to produce a corrected photon count. In some embodiments, the method may further include reconstructing, by image reconstruction circuitry, an image based, at least in part, on the corrected photon count.

In some embodiments of the method, the correcting is configured to correct for pulse pileup. In some embodiments, the trained ANN is trained based, at least in part, on simulated training data. In some embodiments, the incident energy spectrum corresponds to x-ray energy. In some embodiments, the trained ANN is configured to receive a plurality of detected photon counts, each photon count corresponding to a respective energy spectrum.

In some embodiments, the trained ANN is configured to correct the plurality of photon counts to produce a corresponding plurality of corrected photon counts. In some embodiments of the method, the photon counting detector is paralyzable or nonparalyzable. In some embodiments, the ANN is trained based, at least in part, on at most five epochs. In some embodiments, the trained ANN corresponds to a multilayer perceptron.

In some embodiments, a photon count correction system includes a trained artificial neural network (ANN). The trained ANN is configured to receive a detected photon count from a photon counting detector. The detected photon count corresponds to an attenuated energy spectrum. The attenuated energy spectrum is related to characteristics of an imaging object and is based, at least in part, on an incident energy spectrum. The trained ANN is further configured to correct the detected photon count to produce a corrected photon count.

In some embodiments, the photon count correction system includes image reconstruction circuitry configured to reconstruct an image based, at least in part, on the corrected photon count. In some embodiments of the photon count correction system, the correcting is configured to correct for pulse pileup. In some embodiments of the photon count correction system, the trained ANN is trained based, at least in part, on simulated training data. In some embodiments of the photon count correction system, the incident energy spectrum corresponds to x-ray energy.

In some embodiments of the photon count correction system, the trained ANN is configured to capture a plurality of detected photon counts, each photon count corresponding to a respective energy spectrum. In some embodiments of the photon count correction system, the trained ANN is configured to correct the plurality of photon counts to produce a corresponding plurality of corrected photon counts.

In some embodiments of the photon count correction system, the photon counting detector is paralyzable or nonparalyzable.

In some embodiments of the photon count correction system, the ANN is trained based, at least in part, on at most five epochs. In some embodiments of the photon count correction system, the trained ANN corresponds to a multilayer perceptron.

In some embodiments, a computer readable storage device has stored thereon instructions that when executed by one or more processors result in the following operations including receiving, by a trained artificial neural network (ANN), a detected photon count from a photon counting detector. The detected photon count corresponds to an attenuated energy spectrum. The attenuated energy spectrum is related to characteristics of an imaging object and is based, at least in part, on an incident energy spectrum. The operations further include correcting, by the trained ANN, the detected photon count to produce a corrected photon count.

In some embodiments, a computer readable storage device has stored thereon instructions that when executed by one or more processors result in the following operations including any one of the embodiments of the method.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

DETAILED DESCRIPTION

Figure 1:
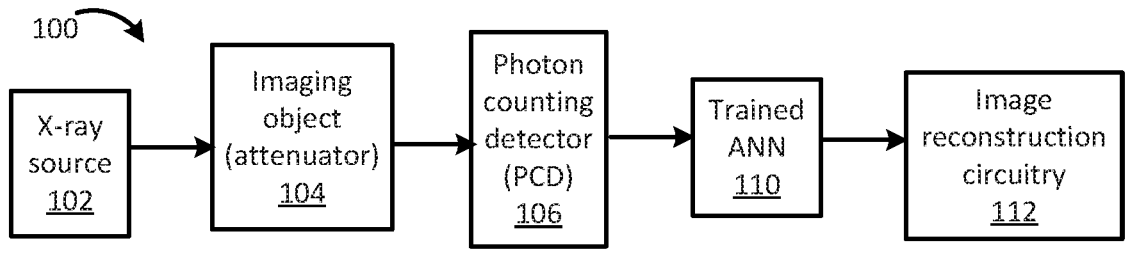
FIG. 1 illustrates a functional block diagram of a photon count correction system consistent with several embodiments of the present disclosure.

The performance of PCDs may be degraded resulting in deviation between the measurement of PCDs and actual values in recorded counts and/or the energy spectra. For example, the time interval between arrival of two consecutive photons is stochastic and the pulses generated by a detector have a finite time duration. Thus, the pulses of two consequent photons may overlap and form a single distorted pulse if the second photon arrives within the pulse duration of the first photon. This phenomenon is called pulse pileup effect (PPE) and may result in both pulse count loss and pulse energy distortion. Pulse pileup effect may worsen as an incident rate of detected pulses increases. For example, operational count rates of some clinical x-ray detectors may be on the order of 100 Mcps/mm$^2$ (million counts per second per square millimeter). If the pulse shape as bipolar with a negative tail, the recorded energy may shift to higher or low level depending on whether the second photon arrives at the positive part of first photon pulse (called peak pileup effect) or at the negative part (called tail pileup effect). Other deviations in PCD measurement from actual counts may include, but are not limited to, charge sharing (where one photon is detected by multiple pixels as two photons with lower energies when its charge cloud interacts with multiple anodes near a pixel boundary), K-escape x-rays, Compton scattering, charge steering, etc. It is contemplated that a system and/or method consistent with the present disclosure may be configured to correct for one or more other deviations in PCD measurement including, but not limited to, charge sharing, K-escape x-rays, Compton scattering, charge steering, etc.

An artificial neural network (ANN) is a network of elements (e.g., nodes) configured to receive input, change their internal state (activation) according to that input, and produce output depending on the input and activation. The network is formed by connecting the output of selected nodes to the input of other nodes to form a directed, weighted graph. The weights as well as the functions that compute the activation can be modified by learning (e.g., training).

A deep neural network is an ANN that has a plurality of layers between the input and output layers. A relationship between the input and the output may be linear or non-linear. A convolutional neural network (CNN) is a type of deep, feed-forward ANN, that includes one or more convolutional layers with fully connected layers on top. A multilayer perceptron (MLP) is a type of feed-forward ANN that includes at least three layers of nodes and each node, except for the input nodes, uses a nonlinear activation function. An MLP may be trained using back propagation, a supervised learning technique. The multiple layers and non-linear activation of an MLP distinguish it from a linear perceptron. CNNs are a type of deep ANN that use a variation of multilayer perceptrons designed to use minimal preprocessing.

A residual neural network is an artificial neural network (ANN) of a kind that builds on constructs known from pyramidal cells in the cerebral cortex. Residual neural networks may utilize skip connections or short-cuts to jump over some layers. A residual neural network may be configured to skip over single layer, may be configured with an additional weight matrix to learn the skip weights, and/or may be configured with a plurality of parallel skips. An adversarial neural network, e.g., a generative adversarial networks (GANs) are a class of artificial intelligence algorithms used in unsupervised machine learning, implemented by a system of two neural networks contesting with each other in a zero-sum game framework.

As used herein, the terms "neural network" and "artificial neural network" (ANN) correspond to an artificial neural network, a deep neural network, a convolutional neural network, a residual neural network, an adversarial neural network and/or a multilayer perceptron.

Deep learning is a type of machine learning technique that uses a cascade of a plurality of layers of nonlinear processing units for feature extraction and transformation. Each successive layer uses the output from the previous layer as input. Deep learning techniques learn in supervised (e.g., classification) and/or unsupervised (e.g., pattern analysis) manners. Deep learning algorithms learn multiple levels of representations that correspond to different levels of abstraction. In other words, deep-learning methods are representation-learning methods with multiple levels of representation, obtained by composing simple but non-linear modules that each transform the representation at one level into a representation at a higher, slightly more abstract level. With the composition of enough such transformations, very complex functions can be learned.

Generally, the present disclosure relates to a photon count correction system that includes a trained artificial neural network (ANN). The trained ANN is configured to correct a photon count received from a photon counting detector. For example, the received photon count may be distorted due to, for example, pulse pileup effects. The corrected photon count may then not include, or may include reduced, effects from pulse pileup. In another example, the received photon count in first energy window (also referred to as an energy bin or an energy channel) may be corrected based, at least in part, on photon counts ("photon count data") in one or more other energy windows.

In one nonlimiting example, the ANN may correspond to a multilayer perceptron. However, the disclosure is not limited in this regard. In one nonlimiting example, the MLP may include three layers, 1024 hidden neurons (i.e., nodes) and may be configured for ReLU (rectified linear unit) activation.

The ANN may be trained based, at least in part, on a training data set that includes a plurality of training pairs. Each training pair may include a detected photon count and corresponding actual photon count. In one nonlimiting example, the training data set may be generated based, at least in part, on a simulated x-ray imaging system. The incident photons may then be represented by a Monte Carlo simulation. Advantageously, the ANN may be trained without determining or identifying a specific model of a detection process and without constraining a corresponding imaging task (e.g., material decomposition, attenuator thickness estimation). The ANN may be relatively simple allowing training in real time and/or convergence in relatively few epochs, e.g., between three and five epochs.

Thus, this disclosure relates to a corrector for photon counting detectors, in particular to, a neural network-based corrector for photon counting detectors. An apparatus, method and/or system are configured to receive a detected photon count from a photon counting detector. The received photon count corresponds to an attenuated energy spectrum. The attenuated energy spectrum is related to characteristics of an imaging object (i.e., "attenuator") and is based, at least in part, on an incident energy spectrum, e.g., produced by an x-ray source. The attenuated spectrum may be further related to characteristics of elements of an x-ray source, e.g., x-ray tube. The apparatus, method and/or system are further configured to correct, by the trained artificial neural network, the detected photon count to produce a corrected photon count. An image may then be reconstructed based, at least in part, on the corrected photon count. As used herein, the terms "imaging object" and "object to be imaged" are used interchangeably and both correspond to "attenuator".

FIG. 1 illustrates a functional block diagram 100 of a photon count correction system consistent with several embodiments of the present disclosure. Photon count correction system 100 may include an x-ray source 102, imaging object (e.g., attenuator) 104 and image reconstruction circuitry 112. Photon count correction system 100 includes a photon counting detector (PCD) 106 and a trained ANN 110. The trained ANN 110 may be trained by a neural network training system, as will be described in more detail below. X-ray source 102 includes a an electrical source and an x-ray tube configured to receive the electrical energy and converting it into two other forms of energy: x-radiation and heat. Thus, x-ray source 102 is configured to provide an x-ray energy spectrum to imaging object 104. Transmitted energy, including a plurality of photons, may then be received by PCD 106. The transmitted energy is configured to represent characteristics of imaging object 104 and is based, at least in part, on the x-ray energy spectrum output from x-ray source 102. PCD 106 is configured to detect the transmitted energy and to count detected photons associated with selected energy spectra (e.g., thresholds corresponding to respective lower thresholds of each of a plurality of energy ranges/bins).

Trained ANN 110 is configured to receive the detected photon count. Trained ANN 110 may then be configured to generate corresponding corrected photon counts based, at least in part, on the received detected photon counts. In one nonlimiting example, the detected photon counts may be corrupted by pulse pileup effects, as described herein. Continuing with this example, trained ANN 110 may be configured to reduce and/or eliminate pulse pileup effects, thus, the corrected photon counts may be relatively more accurate. The correction may be performed without constraining a specific mode of the photon pulse detection process. Image reconstruction circuitry 112 may then be configured to reconstruct an image based, at least in part, on the corrected photon counts. The reconstructed image may then generally not include errors related to pulse pileup effects.

Figure 2A:
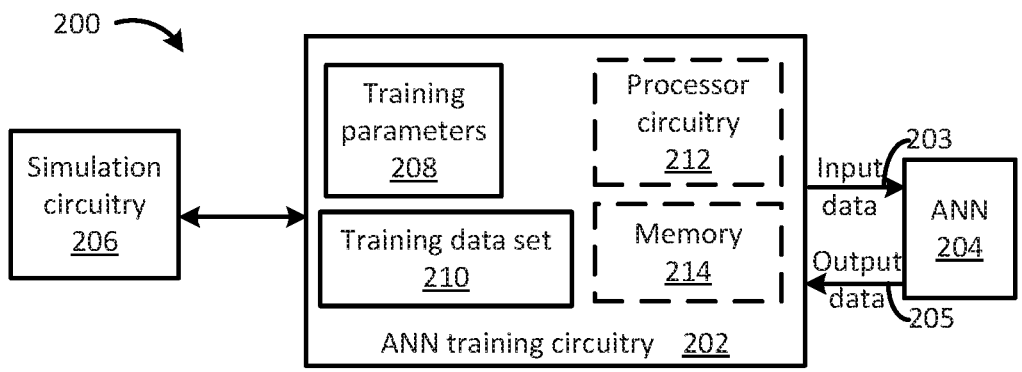
FIG. 2A illustrates a functional block diagram of a neural network training system consistent with several embodiments of the present disclosure.

FIG. 2A illustrates a functional block diagram 200 of a neural network training system consistent with several embodiments of the present disclosure. The neural network training system 200 includes artificial neural network (ANN) training circuitry 202 and an ANN 204. The neural network training system 200 may include simulation circuitry 206. ANN circuitry 202 may include training parameters 208 and training data set 210. ANN training circuitry 202 may further include processor circuitry 212 and/or memory circuitry 214. Processor circuitry 212 may be configured to perform one or more operations of ANN circuitry 202, simulation circuitry 206 and/or ANN 204. Memory 214 may be configured to store information and/or data associated with ANN training circuitry 202, ANN 204 and/or simulation circuitry 206. Memory circuitry 214 may be further configured to store training parameters 208 and/or training data sets 210.

ANN training circuitry 202 is configured to manage training of ANN 204. ANN training circuitry 202 may be configured to provide one or more training parameters to simulation circuitry 206. Training parameters 208 may include, but are not limited to, a number of energy thresholds, spectrum threshold values, trigger threshold values (if any), an incident energy spectrum and/or probability distribution, attenuator characteristics (e.g., thickness (total and individual), material characteristics (e.g., for water, bone, simulated blood), etc.), etc.

The spectrum thresholds correspond to a lower threshold of a selected energy spectrum (i.e., energy bin). Spectrum threshold values are configured to be less than a maximum energy of the x-ray energy spectrum output from the x-ray source, $E_0^{max}$. Thus, as used herein, "spectrum thresholds" are thresholds with values less than $E_0^{max}$.

The trigger thresholds are configured to be greater than or equal to the maximum energy of the x-ray energy spectrum output from the x-ray source, $E_0^{max}$. Qualitatively, input signals with amplitudes greater than or equal to a maximum incident x-ray energy that are detected by a photon counting detector may provide an indication that pulse pileup is occurring. A magnitude of the amplitude may provide an indication of the severity of the pulse pileup effect. Thus, training parameters 208 may include one or more trigger thresholds. Thus, as used herein, "trigger thresholds" are thresholds with values greater than or equal to $E_0^{max}$.

ANN training circuitry 202 may be configured to receive training data from simulation circuitry 206. Training data may include actual photon counts and corresponding detected photon counts for a number of energy spectra and/or attenuators, as will be described in more detail below. The training data set 210 may then include a plurality of pairs of actual photon counts and corresponding detected photon counts.

ANN training circuitry 202 may be configured to provide input data 203 to, and receive output data 205 from, ANN 204. For example, the input data 203 may correspond to detected photon counts and the output data 205 may correspond to corrected photon counts. ANN training circuitry 202 may be configured to train ANN 204, i.e., adjust parameters of ANN 204 to minimize a loss function. In one nonlimiting example, ANN 204 may correspond to an MLP (multilayer perceptron). The MLP may include 3 layers, 1024 hidden neurons (i.e., nodes) and may be configured for ReLU (rectified linear unit) activation. In this example, the ANN 204 may be trained in a relatively short time and may converge in relatively few, e.g., less than five epochs. Of course, other ANN structures may be implemented, consistent with the present disclosure.

Figure 2B:
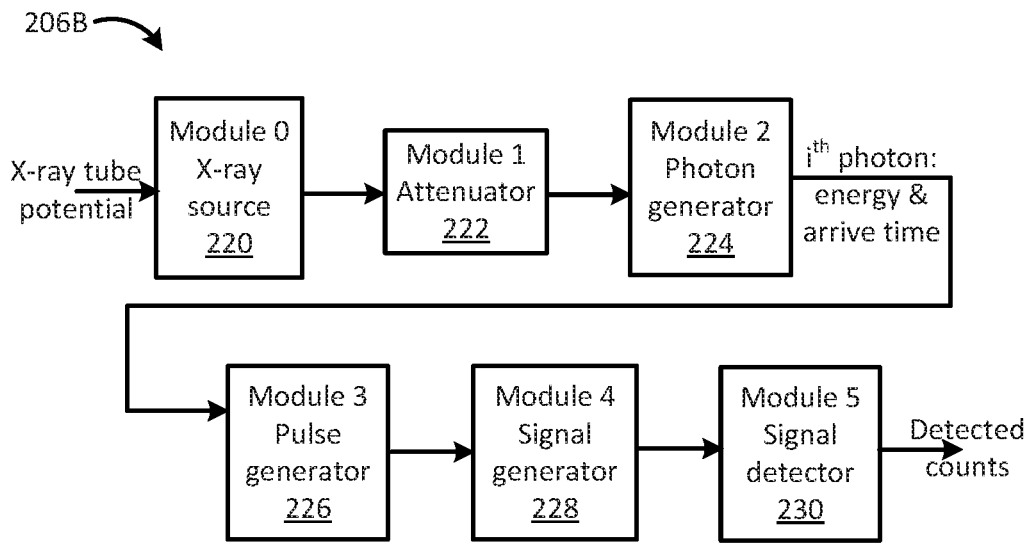
FIG. 2B illustrates a functional block diagram of example simulation circuitry consistent with one embodiment of the present disclosure.

FIG. 2B illustrates a functional block diagram 206B of example simulation circuitry consistent with one embodiment of the present disclosure. Simulation circuitry 206B is one example of simulation circuitry 206 of FIG. 2A. The following description of FIG. 2B may be best understood when considered in combination with FIGS. 3 through 7. Simulation circuitry 206B may include a plurality of modules. Each module is configured to receive an input and to provide an output. A relationship between the output and the input may then correspond to a function in an imaging system from source to detector. Simulation circuitry 206B includes a zeroth module 220, a first module 222, a second module 224, a third module 226, a fourth module 228 and a fifth module 230, as will be described in more detail below.

The zeroth module 220 corresponds to an x-ray source. The zeroth module 220 is configured to receive an x-ray tube potential, $E_0^{max}$, as input and to provide an x-ray energy spectrum, $PMF(E_0)$, as output. The x-ray tube potential, $E_0^{max}$, corresponds to a maximum energy output of an x-ray source, e.g., x-ray source 102. The x-ray energy spectrum corresponds to an incident x-ray spectrum. The energy spectrum may be described as a probability mass function (PMF) with discrete energy windows. For example, the discrete energy windows may have a width of 1 keV (kilo electron volt), centered at integer energy value $E_0$ and with a range of 1 to $E_0^{max}$ keV. In one nonlimiting example, $E_0^{max}=120$ keV.

In an embodiment, the zeroth module 220 may correspond to a source of other radiation. In one nonlimiting example, the zeroth module 220 may correspond to a gamma ray source. In another nonlimiting example, the zeroth module 220 may correspond to a source of infrared light.

Figure 3:
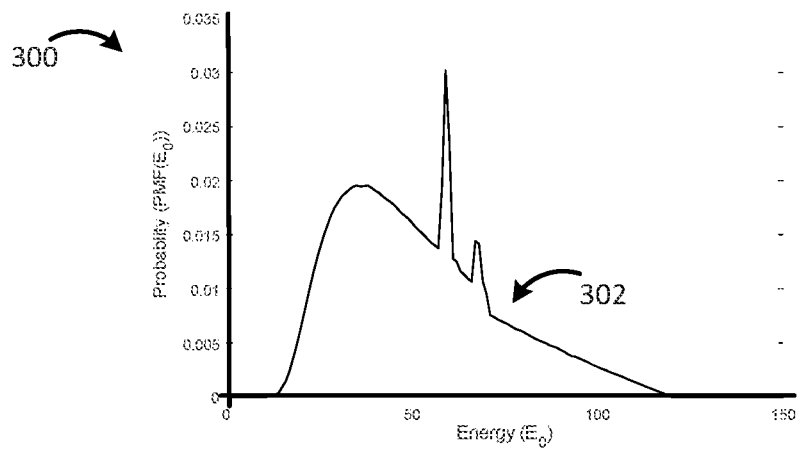
FIG. 3 is a plot illustrating one example simulated x-ray energy spectrum.

FIG. 3 is a plot 300 illustrating one example simulated x-ray energy spectrum 302. The simulated x-ray energy spectrum 302 is one example of an output of the zeroth module 220 of FIG. 2B. A horizontal axis corresponds to energy ($E_0$) and a vertical axis corresponds to probability ($PMF(E_0)$). The simulated x-ray energy spectrum 302 was generated using SPEKTR 3.0, a computational tool for x-ray spectrum modeling and analysis, available from The Mathworks, Natick, Mass. In particular, the simulated x-ray energy spectrum 302 corresponds to a tungsten anode spectral model using interpolating cubic splines ("TASMICS") generated with a 1.6 mm aluminum filter.

Turning again to FIG. 2B, the first module 222 corresponds to an attenuator, i.e., an imaging object (object to be imaged). The first module 222 is configured to receive the x-ray energy spectrum, $PMF(E_0)$, as input from the zeroth module 220 and to provide a transmitted energy spectrum, $PMF(E_1)$, as output to the second module 224. The transmitted energy spectrum (i.e., attenuated energy spectrum) is related to characteristics of the imaging object and is based, at least in part, on the incident energy spectrum, i.e., the x-ray energy spectrum, $PMF(E_0)$. In one nonlimiting example, the attenuator 222 may be modeled as a combination of water, bone and 20% gadolinium-mixed blood and having a thickness, T.

A training data set may be constructed based, at least in part, on a number of combinations of respective thicknesses of water, bone and 20% gadolinium-mixed blood and a corresponding total thickness, T. In this example, the total thickness of material (T) is fixed at 30 cm (centimeters). A thickness of bone (T(bone)) is 0, 1, 3 or 5 cm and a thickness of 20% gadolinium-mixed blood (T(Ga)) ranges from 0 to 20 cm in 4 cm increments. Water may then be added until the total thickness of attenuator is 30 cm (T(water)=T−T(bone)−T(Ga)). Thus, in this example, there are a total of 24 combinations of bone thicknesses, 20% gadolinium-mixed blood thicknesses and water resulting in 24 different attenuators.

Figure 4:
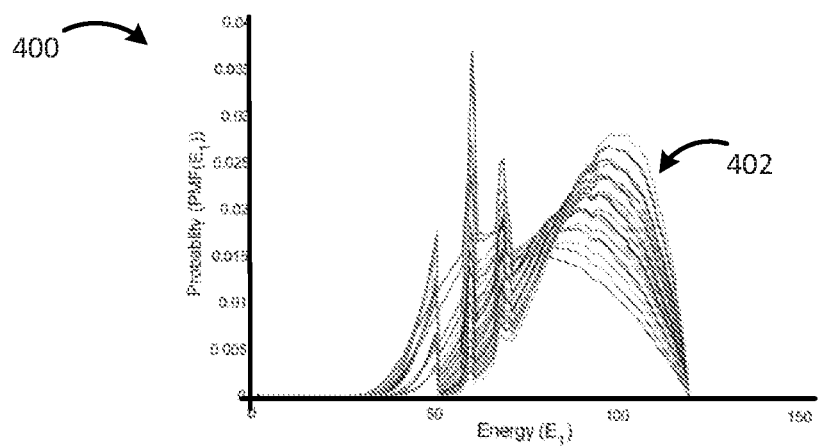
FIG. 4 is a plot illustrating a plurality of transmitted energy spectra, each transmitted spectrum corresponding to an output of a respective attenuator.

FIG. 4 is a plot 400 illustrating a plurality of transmitted energy spectra 402, each transmitted spectrum corresponding to an output of a respective attenuator. Thus, plot 400 includes 24 transmitted spectra 402 with each spectrum corresponding to a respective one of the 24 combinations of bone, 20% gadolinium-mixed blood and water, i.e., the 24 different attenuators. It should be noted that the transmitted energy spectra in the plot 400 have been normalized for ease of visualization. The attenuation coefficients in this example are based on NIST (National Institute of Standards and Technology (U.S. Dept. of Commerce, Gaithersburg, Md.)) reference databases: XAAMDI (X-Ray Attenuation and Absorption for Materials of Dosimetric Interest, 1 keV to 20 MeV) and XCOM (Photon Cross Sections Database, 1 keV to 100 GeV).

Turning again to FIG. 2B, the second module 224 corresponds to a photon generator. The second module 224 is configured to receive the transmitted energy spectrum, $PMF(E_1)$, as input from the first module 222 and to provide a plurality of energies and corresponding arrival times of a plurality of photons as output to the third module 226. Thus, the output corresponds to ($E_i$, $T_i$) where $E_i$ is the energy and $T_i$ is the arrival time of the ith photon. It may be appreciated that i ranges from 1 to N. Reference to the ith photon, ith energy and ith arrival time may refer to any photon of the N arriving photons.

In this example, for one material combination, a number of photons are generated with energies sampled from $PMF(E_1)$. The number of photons follows a Poisson distribution with mean equal to $\Sigma_{E_1=1}^{E_0^{max}} PMF(E_1)*\gamma*\Delta$, where $\gamma$ is incident rate and $\Delta$ is a frame time for one detection process. An interval between arrival times of two consequent photons ($T_{i+1}-T_i$) follows an exponential distribution with mean equal to $1/(\Sigma_{E_1=1}^{E_0^{max}} PMF(E_1)*\gamma)$. In one nonlimiting example, $\gamma$ is set to $10^9$ counts per second per pixel and $\Delta$ is set to 0.5 second.

Turning again to FIG. 2B, the third module 226 corresponds to a pulse generator. The third module 226 is configured to receive the plurality of energies and corresponding arrival times (($E_i$, $T_i$), i=1 ... N) of the plurality of photons as input from the second module 224 and to provide as output to the fourth module 228 a corresponding pulse height (i.e., amplitude) ($P_i(t)$, i=1, ..., N) of each photon at a time, t.

In an embodiment, the pulse generator 226 may be configured to generate one or more of a plurality of pulse types. Pulse types may include, but are not limited to, a delta pulse, a bipolar pulse and/or a unipolar pulse.

Figure 5:
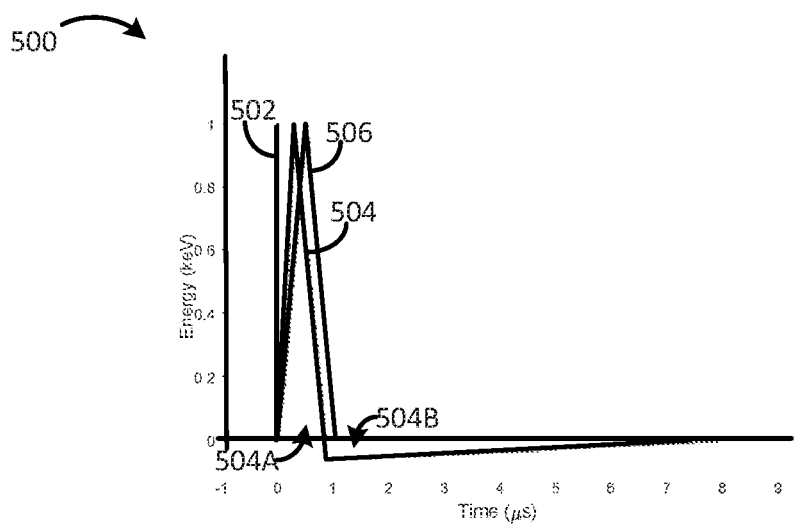
FIG. 5 is a plot illustrating example photon pulse shapes.

FIG. 5 is a plot 500 illustrating example photon pulse shapes. Plot 500 includes a delta pulse 502, a bipolar pulse 504 and a unipolar pulse 506. In the plot 500, the pulses 502, 504, 506 have been normalized for ease of illustration. The bipolar pulse 504 may be implemented as two triangles. A first triangle 504A corresponds to a positive main portion of the bipolar pulse 504 and a second triangle 504B corresponds to a negative tail portion of the bipolar pulse 504. The unipolar pulse 506 may be implemented as a triangle.

Turning again to FIG. 2B, the fourth module 228 corresponds to a signal generator. The fourth module 228 is configured to receive the pulse heights ($P_i(t)$, i=1, ..., N) as input from the third module 226. $P_i(t)$ is the pulse height of the ith photon at time t. The fourth module 228 is configured to provide as output to the fifth module 230 a signal height S(t) a function of time, t. The signal height S(t) may include contributions from a plurality of photon pulses. For example, the signal to be detected may be determined as $S(t)=\Sigma P_i(t)$. As used herein, "height" corresponds to amplitude.

Figure 6:
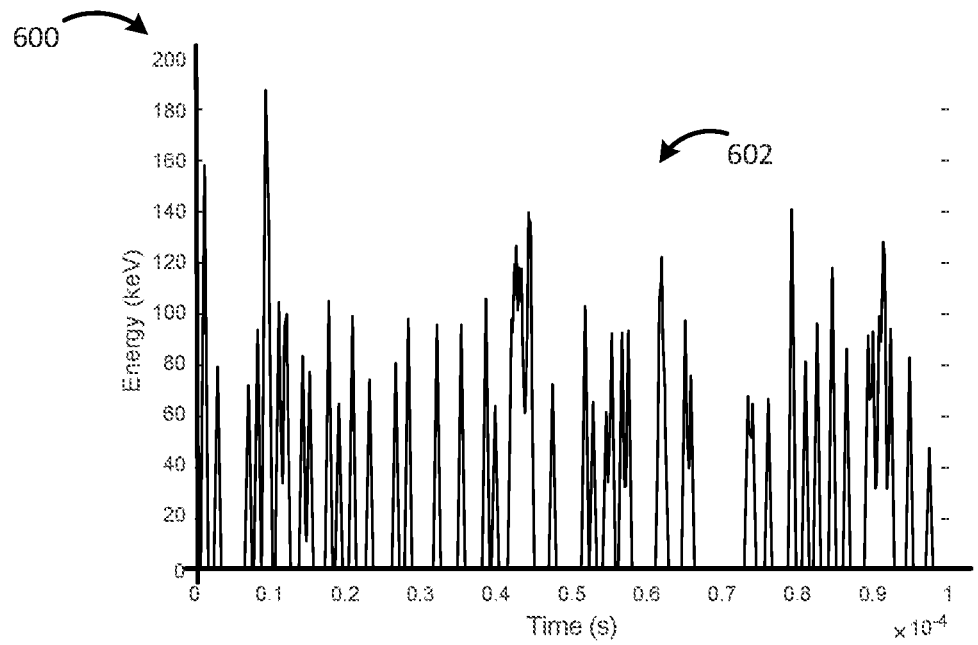
FIG. 6 is a plot illustrating an example input signal (output from a signal generator) that includes a plurality of unipolar pulses.

FIG. 6 is a plot 600 illustrating an example input signal 602 (output from a signal generator) that includes a plurality of unipolar pulses, e.g., pulse 506 of FIG. 5. The horizontal axis is time in seconds and the vertical axis is energy in keV. The input signal may be provided to a signal detector, e.g., the fifth module signal detector 230.

Turning again to FIG. 2B, the fifth module 230 corresponds to a signal detector. The fifth module 230 is configured to receive the signal height S(t) as input from the fourth module 228 and to provide as output one or more detected counts $C_i^{i+1}$ in respective energy windows [i, i+1]. The signal height S(t) may include contributions from a plurality of photon pulses.

In operation, the signal detector 230 has two operating states: active and inactive. For example, if the signal detector 230 is in the active state and a photon arrives, the signal detector 230 is configured to transition to the inactive state. The signal detector 230 may then be configured to remain in the inactive state for a time period (known as "deadtime") of a finite time duration, τ. In one nonlimiting example, τ may be $10^{-6}$ seconds (s), i.e., 1 μs (microsecond). Operation of the signal detector 230 may be characterized according to the contribution to pulse shape of photons that are incident on the detector during deadtime. For example, the signal detector 230 may be characterized as paralyzable or nonparalyzable. It may be appreciated that operation of an actual signal detector may correspond to paralyzable, nonparalyzable or somewhere in between paralyzable and nonparalyzable.

Figure 7:
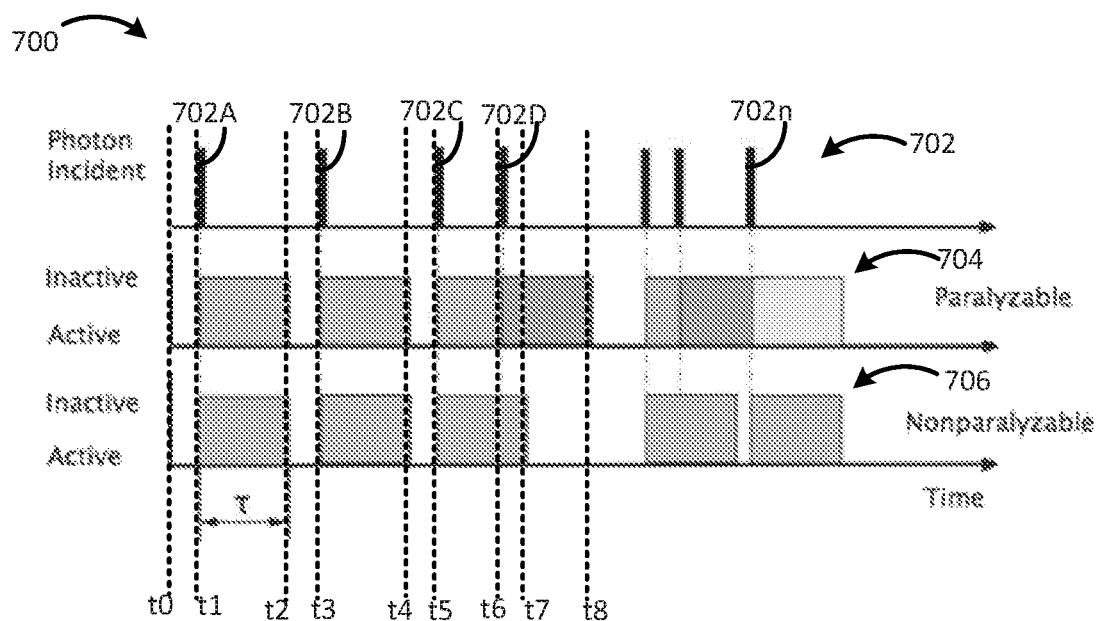
FIG. 7 is a plot illustrating example operation of paralyzable and nonparalyzable photon, i.e., signal, detectors.

FIG. 7 is a plot 700 illustrating example operation of paralyzable and nonparalyzable photon, i.e., signal, detectors. Plot 700 includes a sequence 702 of incident photon pulses 702A, 702B, ... 702n. Plot 700 further includes a sequence of states of a paralyzable detector 704 and a corresponding sequence of states of a nonparalyzable detector 706. The sequences of states of the detectors 704, 706 are related to the sequence 702 of incident photon pulses.

At time t0, both detectors 704, 706 are in the active state. At time t1, a first incident photon 702A arrives. Both detectors 704, 706 transition to the inactive state and remain in the inactive state until time t2, i.e., for duration deadtime, τ. At time t2, both detectors 704, 706 transition to the active state. At time t3 (t3−t1>τ), a second incident photon 702B arrives, both detectors 704, 706 again transition to the inactive state and remain in the inactive state until time t4, i.e., for duration deadtime, τ. At time t4, both detectors transition to the active state. At time t5 (t5−t3>τ), a third incident photon 702C arrives and both detectors again transition to the inactive state.

At time t6 (t6−t5<τ), a fourth incident photon 702D arrives and both detectors 704, 706 remain in the inactive state. At time t7 (t7−t5=τ), the paralyzable detector 704 remains in the inactive state and the nonparalyzable detector 706 transitions to the active state. At time t8 (t8−t6=τ and t8−t7<τ), paralyzable detector 704 transitions to the active state and nonparalyzable detector 706 remains in the active state.

Thus, for a paralyzable detector 704, an inactive state duration time clock is reset when a photon arrives regardless of the initial state (active or inactive) of the paralyzable detector. The inactive state duration time clock is configured to time out at time, τ, (i.e., deadtime from a reset). The paralyzable detector in an inactive state is configured to return to the active state if and only if a time interval between a most recently arrived photon and a next photon is greater than τ. For a nonparalyzable detector, the inactive state duration time clock may not be reset. In other words, a nonparalyzable detector in the inactive state is configured to transition from inactive to active after a time interval τ measured from the transition to the inactive state independent of whether another photon arrives during the deadtime time interval.

In an embodiment, a paralyzable detector may be configured to increment a count associated with an energy threshold when a signal pulse amplitude increases from less than the threshold to greater than the threshold, i.e., rising edge triggered. For example, at least some photon detectors are configured to remain in an inactive state until an amplitude of a received pulse increases from less than the threshold to greater than the threshold.

Operation of a detector may provide an upper bound for a corresponding count if a count resets when the signal height (i.e., amplitude) decreases from greater than a threshold to less than the threshold in contrast to resetting when the signal height increases from less than the threshold to greater than the threshold. In other words, the deadtime loss may be smaller in this case. In another example, the nonparalyzable detectors may be configured to increment the count of one threshold by one after time interval of duration T as long as the height of the pulse is above the threshold.

In one nonlimiting example, the thresholds associated with the fifth module 230 are in the range 1 keV to 240 kV with 1 keV increment. Of course, other combinations of thresholds (i.e., number and corresponding energy level of each) may be implemented, consistent with the present disclosure. The thresholds may include a plurality of spectrum thresholds (i.e., $<E_0^{max}$) and one or more trigger thresholds (i.e., $\geq E_0^{max}$), as described herein. Such variations may be utilized to simulate a variety of detectors and may thus facilitate generating simulation data for training ANN 204 FIG. 2A.

The plurality of pairs of actual counts and detected counts included in training data set 210 may be generated, for example, based, at least in part, on varying attenuator characteristics of the first module 222. The varying attenuator characteristics may then result in a plurality of transmitted energy spectra. The actual counts correspond to the output of the second module (photon generator) 224. The detected counts correspond to the output of the fifth module (signal detector) 230. Thus, a relatively robust training data set 210 may be generated.

The training data set 210 may then be utilized by ANN training circuitry 202 to train ANN 204, as described herein.

Figure 8:
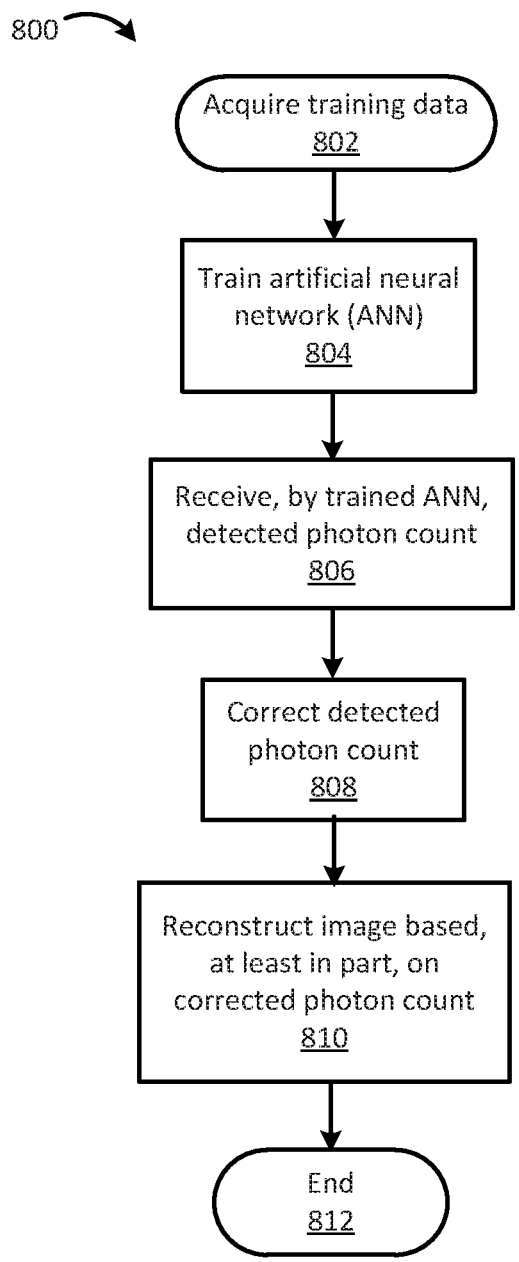
FIG. 8 is an example flowchart of photon count correction operations consistent with several embodiments of the present disclosure.

FIG. 8 is a flowchart 800 of example photon count correction operations consistent with several embodiments of the present disclosure. In particular, flowchart 800 illustrates training an artificial neural network and utilizing the trained ANN to correct a detected photon count. The operations of flowchart 800 may be performed by, for example, neural network training system 200 (e.g., ANN training circuitry 202, ANN 204) of FIG. 2A and/or photon count correction system 100 (e.g., trained ANN 110) of FIG. 1.

Operations of flowchart 800 may begin with acquiring training data at operation 802. An artificial neural network (ANN) may be trained at operation 804. Operation 806 may include receiving, by the trained ANN, a detected photon count. For example, the detected photon count may be received from a photon counting detector. The detected photon count may correspond to an attenuated energy spectrum related to characteristics of an imaging object and based, at least in part, on an incident energy spectrum. The detected photon count may be corrected at operation 808. For example, the detected photon count may be corrected by the trained ANN to produce a corrected photon count. Operation 810 may include reconstructing an image based, at least in part, on the corrected photon count. Program flow may then end at operation 812.

Thus, a neural network may be trained and the trained ANN may then be utilized to correct a detected photon count. For example, correcting the photon count may be configured to reduce or eliminate a pulse pileup effect. Advantageously, the ANN may be trained without determining or identifying a specific model of the detection process. The ANN may be relatively simple, facilitating training in real time and with relatively few epochs for convergence.

EXAMPLE

In this example, generating a training data set using example simulation circuitry 206B and training ANN 204 based, at least in part, on the training data set, are described. In this example, the input x-ray tube potential, $E_0^{max}$, to the zeroth module, x-ray source 220, is 120 keV. The output (i.e., photon pulse) of pulse generator 226 is unipolar and the detector, i.e., signal detector 230, is paralyzable.

One thousand (1,000) trials for each of the 24 attenuation combinations, as described herein, were performed. For each trial, the output of the photon generator 224 and corresponding output of signal detector 230 were captured. A subset of the 24 combinations, e.g., 20 combinations, were then selected. For each of the 20 selected combinations, the trial data was divided into train, validate and test sets with 60%, 20% and 20%, respectively. The remaining 4 combinations were used as a second test set, e.g., Test set 2. The second test set, not used for training, may provide a more robust evaluation of the operation of the photon count correction system, as described herein Four spectrum thresholds and two trigger thresholds were implemented. The spectrum thresholds were [20, 39, 62, 81] keV and in the trigger thresholds were [120, 160] keV. Thus, the inputs correspond to a vector in R and the corresponding outputs are measurements in $R^4$ with 4 spectrum thresholds. The inputs to the ANN were reconstructed from the output of the fifth module, signal detector, 230 and the outputs for comparison to the ANN output were collected by counting the photons generated by the second module, photon generator, 224. In other words, input data 203 corresponded to detected counts output from the fifth module, signal detector 230 and output data 205 was compared to photon energy and arrive time output of the second module, photon generator 224.

ANN 204 was implemented as a three-layer multilayer perceptron with 1024 hidden neurons and ReLU (rectified linear unit) activation. Thus, the example neural network is relatively simple. Hence the training time is relatively fast (e.g., converges within 3-5 epochs). Thus, the training may be performed in real-time.

Figure 9:
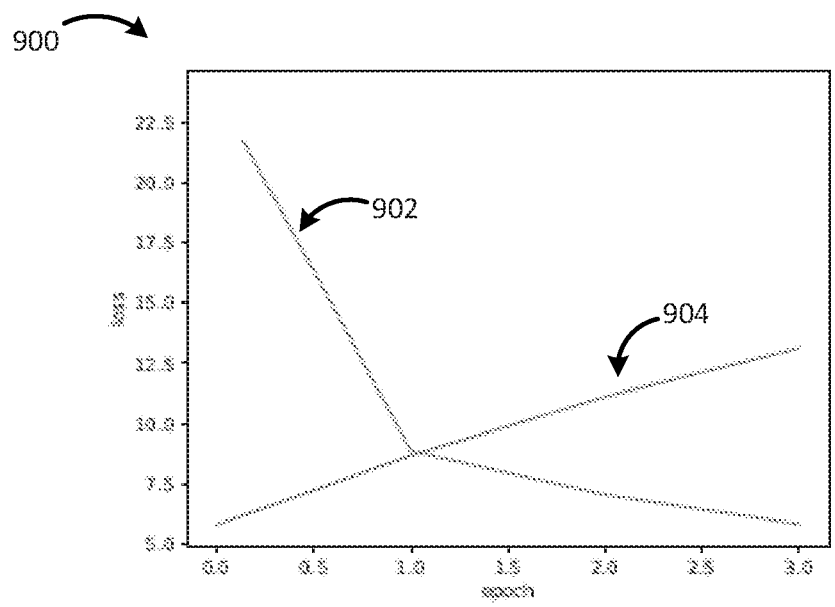
FIG. 9 is a plot illustrating convergence behavior of an artificial neural network, consistent with one embodiment of the present disclosure.

FIG. 9 is a plot 900 illustrating convergence behavior of an artificial neural network, consistent with one embodiment of the present disclosure. The vertical axis is loss and the horizontal axis corresponds to epoch. Plot 900 includes training loss versus epoch 902 and a validation loss versus epoch 904.

Figure 10:
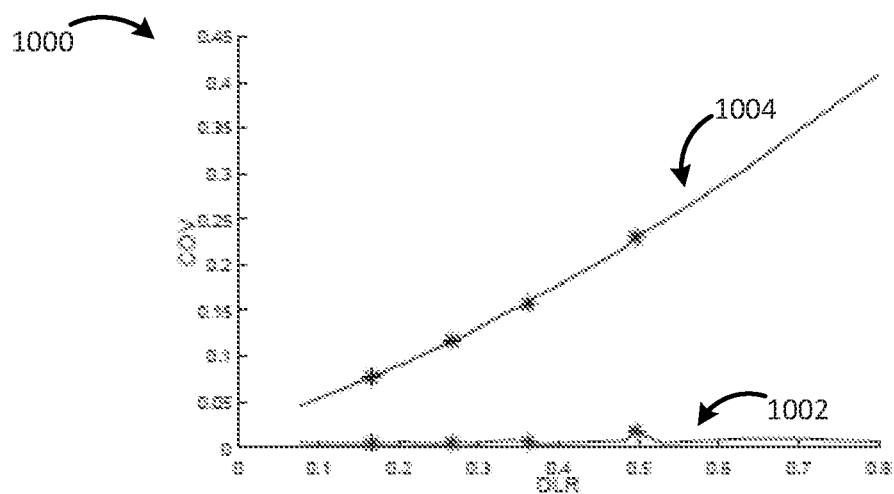
FIG. 10 is a plot illustrating a comparison between a photon count correction system consistent with the present disclosure and a paralyzable detector.

FIG. 10 is a plot illustrating a comparison between a photon count correction system consistent with the present disclosure and a paralyzable detector (i.e., uncorrected photon count). Coefficient of variation (COV) is the metric, which is determined as:

$$COV = RMSD \bigg/ \frac{1}{N}\sum_{i=1}^{N}\sum_{bin=1}^{N_b} n_{true,bin}^i$$

$$RMSD = \sqrt{\frac{1}{N}\sum_{i=1}^{N}\sum_{bin=1}^{N_b} (n_{predict,bin}^i - n_{true,bin}^i)^2}$$

where N is the trial number (N=1,000), $N_b$ is the number of energy spectrum thresholds ($N_b$=4). $n_{predict,bin}^i$ and $n_{true,bin}^i$ are the output of the photon count correction system and the output of the photon generator in the ith trial, respectively. In the plot 900, the vertical axis is COV and the horizontal axis is deadtime loss ratio (DLR). DLR is determined as:

$$DLR_{paralyzable} = 1 - \exp\left(-\gamma * \sum_{E_1=1}^{E_0^{max}} PMF(E_1) * \tau\right)$$

A plot 1002 of COV of the photon count correction system versus DLR illustrates effectiveness of the photon count correction system, consistent with the present disclosure. A plot 1004 of the paralyzable detector output COV versus DLR illustrates an increasing COV with an increasing DLR. The data points on curves 1002 and 1004 correspond to the second test set (Test set 2), as described herein. It may be appreciated that COV is a measure of dispersion of a probability distribution. Thus, a photon count correction system, consistent with the present disclosure, yields a lesser COV compared to the output of a paralyzable detector.

Generally, the present disclosure relates to a photon count correction system that includes a trained artificial neural network (ANN). The trained ANN is configured to correct a photon count received from a photon counting detector. The received (i.e., detected) photon count may be distorted due to, for example, pulse pileup effects. The corrected photon count may then not include, or may include reduced, effects from pulse pileup. The ANN may be trained based, at least in part, on a training data set that includes a plurality of training pairs. Each training pair may include a detected photon count and corresponding actual photon count. In one nonlimiting example, the training data set may be generated based, at least in part, on a simulated x-ray imaging system. Advantageously, the ANN may be trained without determining or identifying a specific model of a detection process and without constraining a corresponding imaging task. The ANN may be relatively simple allowing training in real time and/or convergence in relatively few epochs.

Thus, this disclosure relates to a corrector for photon counting detectors, in particular to, a neural network-based corrector for photon counting detectors. An apparatus, method and/or system are configured to receive a detected photon count from a photon counting detector. The received photon count corresponds to an attenuated energy spectrum. The attenuated energy spectrum is related to characteristics of an imaging object and is based, at least in part, on an incident energy spectrum, e.g., produced by an x-ray source. The apparatus, method and/or system are further configured to correct, by the trained artificial neural network, the detected photon count to produce a corrected photon count. An image may then be reconstructed based, at least in part, on the corrected photon count.

As used in any embodiment herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hardwired circuitry, programmable circuitry such as computer processors including one or more individual instruction processing cores, state machine circuitry, and/or firmware that stores instructions executed by programmable circuitry. The logic may, collectively or individually, be embodied as circuitry that forms part of a larger system, for example, an integrated circuit (IC), an application-specific integrated circuit (ASIC), a field-programmable gate array (FPGA), a programmable logic device (PLD), a complex programmable logic device (CPLD), a system on-chip (SoC), etc.

Processor circuitry 212 may include, but is not limited to, a single core processing unit, a multicore processor, a graphics processing unit, a microcontroller, an application-specific integrated circuit (ASIC), a field programmable gate array (FPGA), a programmable logic device (PLD), etc.

Memory 214 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively memory 214 may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

What is claimed is:

1. A method for x-ray photon count data correction, the method comprising:
    receiving, by an artificial neural network (ANN), a detected photon count from a photon counting detector, corresponding to an attenuated energy spectrum, which is related to characteristics of an x-ray source used for imaging and an object being imaged; and
    correcting, by the ANN, after training, the detected photon count to produce a corrected photon count in an energy window,
    wherein the training comprises training the ANN using parameters including a trigger threshold, and
    wherein the trigger threshold is greater than or equal to a maximum energy of an x-ray energy spectrum output fromm the x-ray source.

2. The method of claim 1, wherein the correcting of the detected photon count in the energy window comprises correcting the detected photon count in the energy window based on respective photon counts in a plurality of energy windows.

3. The method of claim 1, further comprising reconstructing, by image reconstruction circuitry, an image based on the corrected photon count.

4. The method of claim 1, wherein the correcting of the detected photon count comprises correcting for at least one of pulse pileup or a charge sharing effect.

5. The method according to claim 1, wherein at least one of the ANN, the photon counting detector, and the x-ray source is configured based on an x-ray imaging data formation model.

6. The method according to claim 1, wherein the training comprises training the ANN based on simulated training data.

7. The method according to claim 1, wherein the attenuated energy spectrum is based on an incident energy spectrum, which corresponds to radiation energy, x-ray energy, gamma ray or infrared light.

8. The method according to claim 1, wherein the photon counting detector is paralyzable or nonparalyzable.

9. The method according to claim 1, wherein the ANN is trained based on at most five epochs or using a back propagation technique.

10. The method according to claim 1, wherein the ANN corresponds to a multilayer perceptron, a residual neural network or an adversarial neural network.

11. The method of claim 1, wherein the training comprises training the ANN based on training pairs including a detected photon count and a corresponding actual photon count.

12. The method of claim 1, wherein
    the training further comprises training the ANN using training circuitry, which includes an x-ray source module, an attenuator module, a photon generator module, a pulse generator module, a signal generator module, and a signal detector module, and
    the pulse generator module is configured to receive energies and corresponding arrival times of photons from the photon generator module, and output a corresponding pulse height of each of the photons to the signal generator.

13. The method of claim 12, wherein
    the signal generator module is configured to receive the pulse heights, determine a signal height as a function of time by computing a summation of the pulse heights, and output the signal height as a function of time, the signal detector module is configured to receive the signal height, and output detected counts in respective energy windows, and the signal detector module is further configured to transition from an active state to an inactive state, in response to a photon arriving.

14. The method of claim 13, wherein the signal detector module is further configured to return to the active state, in response to a time interval elapsing and an absence of another photon arriving within the time interval, wherein the time interval starts at a time of the photon arriving.

15. The method of claim 1, wherein
the parameters further include spectrum thresholds, and
the spectrum thresholds are less than the maximum energy of the x-ray energy spectrum output from the x-ray source.

16. The method of claim 15, wherein the maximum energy of the x-ray energy spectrum output from the x-ray source is 120 keV.

17. A method for photon count correction, the method comprising:
receiving, by a trained artificial neural network (ANN), a detected photon count from a photon counting detector, the detected photon count corresponding to an attenuated energy spectrum, the attenuated energy spectrum being related to characteristics of an imaging object and based on an incident energy spectrum; and
correcting, by the trained ANN, the detected photon count to produce a corrected photon count in an energy window,
wherein the training comprises training the ANN using parameters including a trigger threshold, and
wherein the trigger threshold is greater than or equal to a maximum energy of an x-ray energy spectrum output from an x-ray source.

18. The method of claim 17, further comprising reconstructing, by image reconstruction circuitry, an image, based on the corrected photon count.

19. The method of claim 17, wherein the correcting of the detected photon count comprises correcting for pulse pileup.

20. The method of claim 17, wherein the trained ANN is trained based on simulated training data.

21. The method of claim 17, wherein the incident energy spectrum corresponds to x-ray energy.

22. The method of claim 17, wherein the trained ANN is configured to receive a plurality of detected photon counts, and each of the detected photon counts correspond to a respective energy spectrum.

23. The method of claim 22, wherein the trained ANN is configured to correct the plurality of detected photon counts to produce a corresponding plurality of corrected photon counts.

24. The method of claim 17, wherein the photon counting detector is paralyzable or nonparalyzable.

25. The method of claim 17, wherein the ANN is trained based on at most five epochs.

26. The method of claim 17, wherein the trained ANN corresponds to a multilayer perceptron.

27. A device comprising means for performing the method according to claim 17.

28. A computer readable storage device having stored thereon instructions that, when executed by one or more processors, cause the one or more processors to perform the method according to claim 17.

29. A photon count correction system comprising:
a trained artificial neural network (ANN) configured to
receive a detected photon count from a photon counting detector, and
correct the detected photon count to produce a corrected photon count in an energy window,
wherein the detected photon count corresponds to an attenuated energy spectrum,
wherein the attenuated energy spectrum is related to characteristics of an imaging object and is based on an incident energy spectrum,
wherein the ANN is trained using parameters including a trigger threshold, and
wherein the trigger threshold is greater than or equal to a maximum energy of an x-ray energy spectrum output from an x-ray source.

30. The system of claim 29, further comprising image reconstruction circuitry configured to reconstruct an image based on the corrected photon count.

31. The system of claim 29, wherein the ANN is further configured to correct the detected photon count in the energy window for pulse pileup.

32. The system of claim 29, wherein the trained ANN is trained based on simulated training data.

33. The system according to claim 29, wherein the incident energy spectrum corresponds to x-ray energy.

34. The system according to claim 29, wherein the trained ANN is further configured to capture a plurality of detected photon counts, each photon count corresponding to a respective energy spectrum.

35. The system of claim 34, wherein the trained ANN is further configured to correct the plurality of photon counts to produce a corresponding plurality of corrected photon counts.

36. The system according to claim 29, wherein the photon counting detector is paralyzable or nonparalyzable.

37. The system according to claim 29, wherein the ANN is trained based on at most five epochs.

38. The system according to claim 29, wherein the trained ANN corresponds to a multilayer perception.

* * * * *